United States Patent [19]

Lau et al.

[11] Patent Number: 4,734,406

[45] Date of Patent: Mar. 29, 1988

[54] 3-PYRIDYLMETHYLNAPHTHYL DERIVATIVES AND COMPOSITION CONTAINING THEM USEFUL TO INHIBIT THROMBOXANE SYNTHETASE

[75] Inventors: Hans-Hermann Lau; Wilhelm Bartmann, both of Bad Soden am Taunus; Gerhard Beck, Frankfurt am Main; Günther Wess, Erlensee, all of Fed. Rep. of Germany

[73] Assignee: Hoechst Aktiengesellschaft, Frankfurt, Fed. Rep. of Germany

[21] Appl. No.: 838,547

[22] Filed: Mar. 11, 1986

[30] Foreign Application Priority Data

Mar. 13, 1985 [DE] Fed. Rep. of Germany ....... 3508903

[51] Int. Cl.$^4$ .................. A61K 31/44; A61K 31/535; C07D 213/55; C07D 413/10
[52] U.S. Cl. ..................... 514/183; 514/188; 514/210; 514/211; 514/212; 514/218; 514/237; 514/238; 514/252; 514/277; 514/318; 514/343; 514/345; 514/350; 514/351; 514/355; 514/357; 540/465; 540/467; 540/470; 540/541; 540/544; 540/575; 544/64; 544/124; 544/131; 544/225; 544/360; 544/365; 546/5; 546/194; 546/275; 546/281; 546/5; 546/194; 546/275; 546/281; 546/298; 546/300; 546/315; 546/333; 546/342; 546/343

[58] Field of Search ............... 546/315, 333, 342, 343, 546/5, 194, 275, 281, 298, 300; 514/277, 355, 357, 183, 188, 210, 211, 212, 218, 237, 238, 252, 318, 343, 345, 350, 351; 540/465, 467, 470, 541, 544, 575; 544/64, 124, 131, 225, 360, 365

[56] References Cited

U.S. PATENT DOCUMENTS 4,496,572 1/1985 Cross et al. ..................... 546/333

Primary Examiner—Henry R. Jiles
Assistant Examiner—Kurt G. Briscoe
Attorney, Agent, or Firm—Finnegan, Henderson, Farabow, Garrett & Dunner

[57] ABSTRACT

Compounds of the formula I

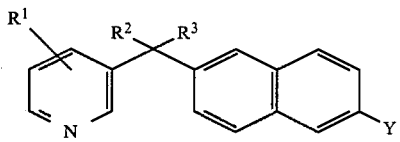

in which $R^1$, $R^2$, $R^3$ and Y have the indicated meanings, their physiologically tolerated acid addition salts, and a process for the preparation of these compounds, are described. The compounds inhibit thromboxane synthetase and can thus be used as medicaments.

4 Claims, No Drawings

3-PYRIDYLMETHYLNAPHTHYL DERIVATIVES AND COMPOSITION CONTAINING THEM USEFUL TO INHIBIT THROMBOXANE SYNTHETASE

3-Substituted pyridine derivatives are inhibitors of thromboxane synthetase (T. Tanouchi, M. Kawamura, I. Ohyama, I. Kajiwara, Y. Iguchi, T. Okada, T. Miyamoto, K. Taniguchi, M. Hayashi, K. Iizuka, M. Nakazawa, J. Med. Chem. 24, 1149 (1981).

The enzyme thromboxane synthetase catalyzes, within arachidonic acid metabolism, the conversion of prostaglandin endoperoxides ($PGH_2$ and $PGG_2$), which induces the aggregation thromboxane $A_2$ ($TXA_2$), which induces the aggregation of blood platelets and furthermore has a powerful constrictive action on smooth muscle. $TXA_2$ plays an essential part in hemostasis, in pathological situations with an increased tendency to vasospasms and/or thrombosis. In addition, $TXA_2$ has a powerful contracting effect on bronchial muscles in vitro and in vivo (B. Samuelsson, Angew. Chem., 95 848 (1983)).

The new 3-pyridylmethylnaphthylcarboxylic acids, their carboxylic acid derivatives and 3-pyridylmethylnaphthylmethanols, which are described in the present invention, are distinguished by specific inhibition of thromboxane synthetase.

Thus they are suitable for the prophylaxis or for the treatment of diseases with a deranged (increased) tendency to platelet aggregation, and where the thromboxane levels are pathologically increased, which are found in association with ischemia, angina pectoris, thromboembolic disorders, atherosclerosis, coronary spasms, arrhythmias, cerebral ischemic attacks, migraine and other vascular headaches, myocardial infarct, hypertension, breathing disturbances such as asthma and apnea, inflammatory diseases and microvascular complications associated with diabetes mellitus. Moreover, the compounds are suitable for slowing down or for preventing the proliferation of tumor cells.

Derivatives of 3-pyridylmethylnaphthalene and 3-pyridylcarbonylnaphthalene dervatives have already been disclosed in European Pat No. A2-0 073 663.

The present invention relates to new 3-pyridylmethylnaphthylcarboxylic acids, to their carboxylic acid derivatives, and to 3-pyridylmethylnaphthylmethanols of the formula I

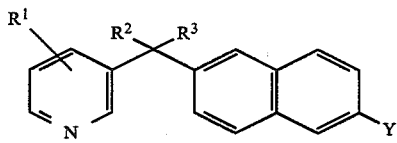

and to the physiologically tolerated acid addition salts.
In the general formula I:
$R^1$ denotes hydrogen, or, in the 2-, 4-, 5- or 6-position, halogen, a straight-chain or branched alkyl radical having 1-6 carbon atoms, a cycloalkyl radical having 3-7 carbon atoms, a phenyl-$C_1$-$C_2$-alkyl radical or a phenyl radical, each of which can be substituted 1-3 times in the nucleus by halogen, alkyl and/or alkoxy, each having 1-6 carbon atoms, or denotes a hydroxyl radical or an alkoxy radical having 1-6 carbon atoms, $R^2$ denotes hydrogen, a hydroxyl radical, halogen, an alkoxy radical having 1-6 carbon atoms, or a phenoxy radical which can be substituted 1-3 times in the nucleus by halogen, trifluoromethyl, alkyl and/or alkoxy, each having 1-6 carbon atoms, $R^3$ denotes hydrogen, a cycloalkyl radical having 3-7 carbon atoms, a straight-chain or branched alkyl radical having 1-8 carbon atoms, a straight-chain or branched unsaturated aliphatic hydrocarbon radical having up to 8 carbon atoms and up to 3 double or triple bonds, a phenyl radical which can be substituted 1-3 times in the nucleus by halogen, trifluoromethyl, hydroxyl, alkyl and/or alkoxy, each having 1-6 carbon atoms, or denotes a 2-, 3- or 4-pyridyl radical which can be substituted in the 4- or 5-position by $C_1$-$C_4$-alkyl, or $R_2$ and $R_3$ together denote oxygen, an N—$R^4$ group or an N—O—$R^4$ group, $R^4$ denoting hydrogen, a straight-chain or branched alkyl radical having up to 6 carbon atoms, which in turn can be substituted with cycloalkyl having 3-8 carbon atoms, carboxyl, carbalkoxy having up to 6 carbon atoms or a phenyl radical which in turn can be substituted 1-3 times in the nucleus by halogen, trifluoromethyl, alkyl or alkoxy having up to 6 carbon atoms, or a phenyl radical which can be substituted 1-3 times in the nucleus by halogen, trifluoromethyl, alkyl or alkoxy having up to 6 carbon atoms, Y denotes a radical of the formula $CO_2R^5$,

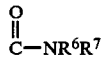

or $CH_2OH$, $R^5$ denoting hydrogen, a straight-chain or branched alkyl radical having up to 8 carbon atoms, a straight-chain or branched unsaturated aliphatic hydrocarbon radical having up to 6 carbon atoms, a cycloaliphatic hydrocarbon radical having 3 to 7 carbon atoms, an araliphatic hydrocarbon radical having 7 to 10 carbon atoms, or a physiologically tolerated metal ion, $NH_4$ ion or an ammonium ion which is derived from a primary, secondary or tertiary amine, or a tetraalkylammonium ion, $R^6$ denoting hydrogen, a straight-chain or branched alkyl radical having 1-6 carbon atoms, a cycloaliphatic hydrocarbon radical having 3-7 carbon atoms, an araliphatic hydrocarbon radical which has 7-10 carbon atoms and can be substituted 1-3 times in the nucleus by halogen, trifluoromethyl, alkyl and/or alkoxy, each having 1-6 carbon atoms, or denoting a phenyl radical which can be substituted 1-3 times in the nucleus by halogen, trifluoromethyl, alkyl and/or alkoxy, each having 1-6 carbon atoms, $R^7$ denoting hydrogen, a straight-chain or branched alkyl radical having 1-6 carbon atoms, or $R^6$ and $R^7$ together denoting a —$(CH_2)_n$— group with n=3-6, or a —$(CH_2)_p$—Z—$(CH_2)_p$— group with p=2 or 3, Z being oxygen or N—$R^8$, $R^8$ denoting hydrogen or a straight-chain or branched alkyl radical having 1-6 carbon atoms, with the exception of the compounds of the formula I in which, when Y denotes the radicals -$CONH_2$ or $COOR^5$, with $R^5$ denoting hydrogen or $C_1$-$C_6$-alkyl, $R^1$, $R^2$ and $R^3$ represent hydrogen, or $R^1$ represents hydrogen and $R^2$ and $R^3$ together represent oxygen.

The particularly preferred substituents $R^1$ are:

Hydrogen or, in the 4- or 5-position, halogen, a straight-chain or branched alkyl radical having 1–6 carbon atoms, in particular $C_1$–$C_4$-alkyl, or a cycloaliphatic hydrocarbon radical having 5–7 carbon atoms, in particular $C_5$–$C_7$-cycloalkyl.

The particularly preferred substituents $R^2$ are:

Hydrogen, hydroxyl, halogen, alkoxy having 1–4 carbon atoms, or a phenoxy radical which is preferably unsubstituted in the nucleus or is substituted 1–2 times by $C_1$–$C_3$-alkyl, in particular methyl or ethyl, by $C_1$–$C_3$-alkoxy, in particular methoxy or ethoxy, by halogen or by trifluoromethyl. The particularly preferred substituents $R^3$ are: Hydrogen, straight-chain or branched alkyl having 1–6 carbon atoms, a cycloalkyl radical having 5–7 carbon atoms, in particular $C_5$–$C_7$-cycloalkyl, or a phenyl radical which is unsubstituted in the nucleus or is substituted 1–2 times by $C_1$–$C_3$-alkyl, in particular methyl or ethyl, hydroxyl, $C_1$–$C_3$-alkoxy, in particular methoxy or ethoxy, halogen or by trifluoromethyl, or 3-pyridyl which can be substituted in the 4- or 5-position by $C_1$–$C_3$-alkyl, in particular methyl or ethyl.

Furthermore, preferred compounds of the formula I are those in which $R^2$ and $R^3$ together represent oxygen or an N—$OR^4$ group, the particularly preferred substituents $R^4$ being: hydrogen, straight-chain or branched alkyl having 1–4 carbons atoms which in turn can be substituted with carboxyl, $C_1$–$C_3$-alkoxycarbonyl, in particular with methoxycarbonyl or ethoxycarbonyl, or with phenyl.

The preferred meaning of Y is $CO_2R^5$,

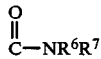

or $CH_2OH$, the following being suitable meanings which are preferred for $R^5$, $R^6$ and $R^7$:

$R^5$: hydrogen, straight-chain or branched alkyl having up to 6 carbon atoms, in particular $C_1$–$C_4$-alkyl, a straight-chain or branched unsaturated, aliphatic hydrocarbon radical having up to 4 carbon atoms, in particular $C_2$–$C_4$-alkenyl, a cycloaliphatic hydrocarbon radical having 5–7 carbon atoms, in particular $C_5$–$C_7$-cycloalkyl, an araliphatic hydrocarbon radical having 7–10 carbon atoms, in particular phenethyl or benzyl, or a physiologically tolerated metal ion, $NH_4$ ion or an ammonium ion which is derived from a primary, secondary or tertiary amine, in particular:

Hydrogen, methyl, ethyl, n-butyl, n-pentyl, n-hexyl, n-heptyl, 2-propyl, 2-butyl, 2-pentyl, 3-hexyl, 2-methylpropyl, 2-methylbutyl, 4,4-dimethylpentyl, 5,5-dimethylhexyl, cyclopentyl, cyclohexyl, cycloheptyl, methylammonium, dicyclohexylammonium and tris(hydroxymethyl)methylammonium.

$R^6$: hydrogen, straight-chain or branched alkyl having up to 6 carbon atoms, in particular $C_1$–$C_4$-alkyl, a cycloaliphatic hydrocarbon radical having 5–7 carbon atoms, in particular cyclopentyl and cyclohexyl, an araliphatic hydrocarbon radical having 7–10 carbon atoms, in particular benzyl and 2-phenylethyl, or a phenyl radical.

$R^7$: hydrogen, straight-chain or branched alkyl having 1 to 4 carbon atoms.

$R^6$ and $R^7$ can together, preferably, denote:
a —$(CH_2)_n$— group with $n=4$ or 5, or a —$(CH_2)_2$—O—$(CH_2)_2$— group.

Particularly preferred compounds of the formula I are those in which $R^1$ denotes hydrogen or $C_1$–$C_2$-alkyl or phenyl in the 4-position, $R^2$ denotes hydrogen, hydroxyl, $C_1$–$C_2$-alkoxy or chlorine, $R^3$ denotes hydrogen or $C_1$–$C_2$-alkyl, and Y denotes the $COOR^5$ group, with $R^5$ denoting H or $C_1$–$C_4$-alkyl, and the physiologically tolerated acid addition salts.

The invention also relates to the acid addition salts of the compounds which have been described with inorganic or organic acids, for example hydrochloric acid, hydrobromic acid, sulfuric acid, phosphoric acid, nitric acid, acetic acid, propionic acid, oxalic acid, malonic acid, glycollic acid, succinic acid, maleic acid, fumaric acid, tartaric acid, citric acid, benzoic acid or cinnamic acid.

The invention also relates to a process for the preparation of compounds of the formula I, which comprises (a) selective metallation in the 3-position of a compound of the formula II

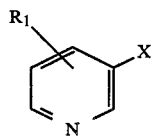

in which
$R^1$ has the meaning indicated for formula I, and
X denotes chlorine, bromine or iodine, followed by a reaction with a compound of the formula III

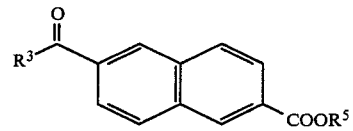

in which
$R^3$ has the meaning mentioned for formula I, and
$R^5$ denotes $C_1$–$C_8$-alkyl, to give a compound of the formula I in which $R^2$ represents hydroxyl, and Y represents the group —$COOR^5$ with $R^5$ representing $C_1$–$C_8$-alkyl, (α) optionally, selective halogenation of the resulting compound to give a compound of the formula I in which $R^2$ denotes halogen, and Y denotes the group —$COOR^5$ with $R^5$ denoting $C_1$–$C_8$-alkyl, (β) optionally, reduction of a compound of the formula I, in which $R^2$ represents halogen, and Y represents the group —$COOR^5$ with $R^5$ representing $C_1$–$C_8$-alkyl, to give a compound of the formula I in which $R^2$ represents hydrogen, and Y represents the group —$COOR^5$ with $R^5$ representing $C_1$–$C_8$-alkyl, or (γ) optionally, initial dehydration followed by catalytic hydrogenation of a compound of the formula I, in which $R^2$ denotes hydroxyl, $R^3$ denotes primary or secondary alkyl, and Y denotes the group —$COOR^5$ with $R^5$ denoting $C_1$–$C_8$-alkyl, to give a compound of the formula I in which $R^2$ denotes hydrogen, $R^3$ denotes alkyl, and Y denotes the group —COOR$^5$ with $R^5$ denoting $C_1$–$C_8$-alkyl, (δ) optionally, reaction of a compound of the formula I, in which $R^2$ represents halogen, and Y represents the group —COOR$^5$ with $R^5$ representing $C_1$–$C_8$-alkyl, with a compound of the formula IV $$R^9\text{—OH} \qquad \text{IV}$$

in which $R^9$ represents $C_1$–$C_6$-alkyl or a phenyl radical which can be substituted in the nucleus 1–3 times by halogen, trifluoromethyl, alkyl and/or alkoxy having 1–6 carbon atoms, in the presence of a base, to give a compound of the formula I in which $R^2$ represents the group —OR$^9$, and Y represents the group —COOR$^5$ with $R^5$ representing $C_1$–$C_8$-alkyl, or (b) selective metallation in the 2-position of a compound of the formula V

V followed by reaction with a compound of the formula VI in which

VI in which
$R^1$ and $R^3$ have the meanings indicated for formula I, to give a compound of the formula VII

VII and (i) oxidation of a compound of the formula VII, in which $R^1$ and $R^3$ have the meaning indicated for formula I, but $R^3$ is not hydrogen, to give a compound of the formula I in which $R^2$ represents the hydroxyl group, and Y represents the carboxyl group, (ii) oxidation of a compound of the formula VII, in which $R^1$ has the meaning indicated for formula I, and $R^3$ denotes hydrogen, to give a compound of the formula I in which $R^2$ and $R^3$ together represent oxygen, and Y represents the carboxyl group, and, optionally, reaction with a hydroxylamine of the formula $H_2NOR^4$, or with an amine of the formula $H_2NR^4$, in which $R^4$ has the meanings mentioned for formula I, to give a compound of the formula I in which $R^2$ and $R^3$ together denote the group —NOR$^4$ or —NR$^4$, (iii) initial protection, with a protective group, of the hydroxyl group in a compound of the formula VII, in which $R^1$ has the meaning indicated for formula I, and $R^3$ denotes hydrogen, then oxidation of the compound and, finally, elimination of the protective group again, thus obtaining a compound of the formula I in which $R^2$ represents the hydroxyl group, $R^3$ represents hydrogen, and Y represents the carboxyl group, (iv) initial dehydration followed by catalytic hydrogenation of a compound of the formula VII, in which $R^1$ has the meaning mentioned for formula I, and $R^3$ denotes primary or secondary alkyl, to give a compound of the formula VIII

VIII in which $R^1$ and $R^3$ have the abovementioned meanings, or selective halogenation of a compound of the formula VII to give a compound of the formula IX

IX in which $R^1$ and $R^3$ have the meanings mentioned for formula 1, and

Hal represents chlorine, bromine or iodine, and either reduction of the resulting compound to give a compound of the formula VIII

VIII or reaction of the resulting compound with a compound of the formula IV $$R^9\text{—OH} \qquad \text{IV}$$

in which $R^9$ represents $C_1$–$C_6$-alkyl or an aryl radical which can be substituted in the nucleus 1–3 times by halogen, trifluoromethyl, alkyl and/or alkoxy having 1–6 carbon atoms, in the presence of a base, to give a compound of the formula X

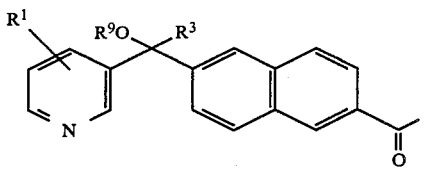

and oxidation of a resulting compound of the formula VIII, IX or X to give a compound of the formula I in which $R^1$ and $R^3$ have the meanings mentioned above for formula I, Y represents the carboxyl group, and $R^2$ denotes halogen, hydrogen or the group $OR^9$, and, optionally, conversion of a compound of the formula I, obtained by process (a) or (b), in which Y represents carboxyl or alkoxycarbonyl, into the corresponding esters, amides or salts, or reduction to give a compound of the formula I in which Y denotes the group —CH$_2$OH.

The 2-bromonaphthalene derivative of the formula V which is used as starting material in the process b) according to invention can be synthesized by processes known from the literature from 6-acetyl-2-bromonaphthalene, which can in turn be obtained by the method of R. B. Girdler, P. H. Gore, J. A. Hoskins, J. Chem. Soc. (C), 1966, 518.

3-Acetylpyridines of the general formula VI can be prepared by the process described in Heterocyclic Compounds, Pyridine and its Derivatives, part 4, pages 123 et seq., 1964 (New York, London, Sidney), but in particular also by the method of J. Cason, Chem. Reviews, 40, 15 (1947).

The synthesis of 3-halogenated pyridine derivates (process a) of the general formula II is carried out by, inter alia, the processes described in Bull. Soc. Chim. Fr., 1972, 2466 and Bull. Soc. Chim. Fr., 1976, 530.

6-Formyl-2-naphthoic esters of the formula III can be synthesized by the process described in German Offenlegungsschrift No. 2,363,416. Other starting compounds of the general formula III, with $R^3$=hydrogen, can be prepared from the 6-formyl-2-naphthoic esters in analogy to methods known from the literature.

O-substituted hydroxylamines can be prepared from N-hydroxyphthalimide by the process described in Houben-Weyl, vol. x/1, page 1192, and W. B. Lutz, J. Org. Chem., 36, 3835 (1971).

Methods for the preparation of metallated products from compounds of the general formula II or V have been described for the lithium derivatives (U. Schöllkopf in Houben-Weyl, vol. XIII/1, pages 3 et seq. and 87 et seq.), for the magnesium derivatives (K. Nutzel in Houben-Weyl, vol. XIII/2, pages 47 et seq.) and for the titanium derivatives (B. Weidmann, D. Seebach, Angew. Chem. 95, 12 (1983)).

Particularly suitable for the preparation of compounds of the formula I with $R^2$=halogen, and of compounds of the formula IX, are the reactions of the corresponding hydroxyl compounds of the formulae I and VII respectively with thionyl chloride (see Houben-Weyl, vol. V/3, page 862) or with triphenylphosphine/-tetrachloromethane (E. I. Snyder, J. Org. Chem., 37, 1466 (1972)).

The ketones of the formula VII, VIII and X can be oxidized in a haloform reaction with chlorine, bromine or iodine, in the presence of a strong base such as, for example, sodium or potassium hydroxide, to give compounds of the formula I in which Y denotes a carboxyl group.

It is possible by processes known from the literature to prepare from compounds of the formula I with Y=carboxyl or alkoxycarbonyl the corresponding esters, amides and salts.

The reduction of the ester or acid group in compounds of the formula I to give compounds of the formula I with Y=CH$_2$OH is accomplished with, inter alia, complex metal hydrides such as lithium alanate or sodium boranate in a suitable inert solvent.

The compounds of the general formula I exhibit a specific inhibition of thromboxane synthetase and can thus be used as medicaments for the prophylaxis or treatment of diseases with a deranged, ie. increased, tendency of the platelets to aggregate, as well as when the thromboxane levels are pathologically increased, which are found in association with ischemia, angina pectoris, thromboembolic disorders, atherosclerosis, coronary spasms, arrhythmias, cerebral ischemic attacks, migraine and other vascular headaches, myocardial infarct, hypertension, breathing disturbances such as asthma or apnes, inflammatory disorders and microvascular complications associated with diabetes mellitus. The compounds according to the invention exert a favorable effect on disorders with increased thromboxane levels in various organs, for example in the region of the kidneys or the stomach and intestines associated with colitis or inflammatory bowel disease. The compounds are, moreover, suitable for slowing down, or even preventing, the proliferation of tumor cells.

The compounds are active in doses of 0.01 mg/kg to 10 mg/kg. The single dose administered can be between 1 mg and 500 mg. The preferred daily dose on oral administration is between 1 mg and 1 g.

The metabolites of arachidonic acid are involved in a number of physiological and pathophysiological processes. Prostacyclin (PGI$_2$) and thromboxane A$_2$ (TXA$_2$) are of essential importance in the regulation of the tone of blood vessels and of platelet aggregation. Prostacyclin, which is formed from prostaglandin endoperoxide H$_2$ (PGH$_2$) preferentially in the endothelial cells of the blood vessels, brings about vasodilatation and simulataneously prevents the aggregation of platelets. The conversion of PGH$_2$ into prostacyclin is catalyzed by prostacyclin synthetase. The physiological antagonist of prostacyclin is thromboxane A$_2$, which is synthesized from PGH$_2$ mainly in the blood platelets. This reaction is catalyzed by the enzyme thromboxane synthetase. TXA$_2$ brings about aggregation of blood platelets and results in vasoconstriction. It is the most potent vasoconstrictor hitherto known in the human body (see A. G. Herman, P. M. Vonhoutte, H. Denolin, A. Goossens, Cardiovascular Pharmacology of the Prostaglandins, Raven Press, New York, 1982). Disturbances of the equilibrium between prostacyclin and thromboxane $A_2$ result in pathophysiological situations. Thus, when the $PGI_2$ levels remain the same, an increase in the thromboxane level results in aggregation of blood platelets and in vasospasms as well as in an increased susceptibility to atherothrombosis (Lancet 1977, 479; Science 1976, 1135; Amer. J. Cardiology 41, 787 (1978); Lancet 1977, 1216).

In experimental atherosclerosis, the formation of $PGI_2$ is inhibited with, at the same time, an increase in the formation of thromboxane $A_2$ (Prostaglandins 14, 1025 and 1035 (1977)). For this reason, $TXA_2$ is thought to be connected with various types of angina, the development of myocardial infarcts, sudden heart death and strokes (Thromb. Haemostasis 38, 132 (1977); Platelets, Prostaglandins and Cardiovascular System, Florence, February 1984).

Another area in which a disturbance of the $PGI_2/TXA_2$ equilibrium is regarded as being a contributory factor is migraine. Migrainous headaches are linked with changes in the intracerebral and extracerebral blood flow, in particular with a reduction in the cerebral blood flow taking place before the manifestation of the headache and with subsequent dilatation in both vascular areas during the headache phase. Platelets from migraine patients have a greater tendency to aggregate than do those from normal individuals (J. clin. Pathol. 24, 250 (1971); J. Headache, 17, 101 (1977); Lancet 1978, 501).

In patients with diabetes mellitus, an imbalance between prostacyclin and thromboxane $A_2$ is regarded as being the cause of the microvascular complications. Platelets from diabetes patients form increased amounts of $TXA_2$ and malondialdehyde (Symposium "Diabetes and Thrombosis—Implications for Therapy", Leeds, Great Britain, April 1979). It has also been shown that, in rats with experimentally induced diabetes, the vascular $PGI_2$ formation is inhibited whereas the $TXA_2$ synthesis in the platelets is increased (IV. Int. Prostaglandin Conference, Washington DC, May 1979).

Non-steroidal antiinflammatory agents inhibit cyclooxygenase, which catalyzes the conversion of arachidonic acid into $PGH_2$ via $PGG_2$. Thus they intervene both in the biosynthesis of thromboxane $A_2$ and in that of prostacyclin. Thus, more valuable compounds would be those which specifically block the formation of thromboxane $A_2$ by inhibition of thromboxane synthetase and, at the same time, have no effect on the formation of prostacyclin.

REPORT OF EXPERIMENTS

The biochemical and pharmacological activities were determined in the following test systems:

1. Inhibition of the arachidonic acid-induced aggregation of human platelets in vitro.

Blood is taken, by careful cannulation of the antecubital vein, from apparently healthy male and female volunteers, who have taken no medicaments in the preceding 10-day period, and is immediately stabilized with sodium citrate (ad. 0.38%). Platelet-rich plasma (PRP) is obtained in the supernatant by centrifugation at $140 \times g$ for 15 minutes, and the platelet content of this should be in the range $2.5 - 3.5 \times 10^8$/ml (Coulter counter). The platelet aggregation is followed optically by measurement of the transmission of light in a Born aggregometer. The total volume of the test mix is 0.25 ml. The preincubation time at 37° C. with the test product is 10 min, and aggregation is then induced with $2 \times 10^{-4}$ M arachidonic acid. The test product is, as a rule, tested in five different concentrations in the PRP from three different donors. Dose-effect curves are drawn from the maximal aggregation amplitudes in each case, and the $IC_{50}$ values are determined graphically. ($IC_{50}$ is the concentration which brings about 50% inhibition of the arachidonic acid-induced aggregation). The measurements are carried out in the period 1-6 hours after blood sampling.

The following $IC_{50}$ values for the inhibition of the arachidonic acid-induced aggregation of human platelets in vitro were determined by the method described above for the compounds according to the invention:

| Example | $IC_{50}$ value (mol/l) |
|---|---|
| 8 | $6.3 \times 10^{-6}$ |
| 9 | $1.7 \times 10^{-6}$ |

2. Thrombin-induced $TXA_2$ release in platelet-rich human plasma in vitro

Blood is taken, by careful cannulation of the antecubital vein, from apparently healthy male and female volunteers, who have taken no medicaments in the preceding 10-day period, and is immediately stabilized with sodium citrate (ad. 0.38%). Platelet-rich plasma (PRP) is obtained in the supernatant by centrifugation at $140 \times g$ for 15 minutes, and the platelet content of this should be in the range $2.5 - 3.5 \times 10^8$/ml. The platelets are sedimented by renewed centrifugation (10 min at $2,000 \times g$), and then resolubilized in Tyrode's solution (about $7 \times 10^7$ platelets/ml, total volume per measurement 0.5 ml). After addition of test substance, the mixture is incubated at 37° C. for 10 min, and then $7.2 \times 10^{-7}$ M arachidonic acid and 0.5 U thrombin are added, and incubation is carried out at 37° C. for 30 min. This is stopped in an ice bath and, after addition of tracer and $TXB_2$-specific antibodies (NEN, Dreieich), the $TXB_2$ content is determined radioimmunologically ($TXA_2$ is unstable under the experimental conditions and thus cannot be measured. The stable hydrolysis product $TXB_2$ is measured in its place). The measured variable is the relative $TXB_2$ content in the platelet incubations from two or three different donors with and without (=100%) the test substance.

The following figures for the $TXB_2$ release after administration of $10^{-6}$ and $10^{-7}$ mol/l respectively of the test substance were determined, for example, for the compounds according to the invention by the method described above

| Example | $TXB_2$ release |
|---|---|
| 8 | $10^{-6}$ mol/l: 13% |
|   | $10^{-7}$ mol/l: 88% |
| 9 | $10^{-6}$ mol/l: 21% |

-continued

| Example | TXB₂ release |
|---------|--------------|
|         | $10^{-7}$ mol/l: 64% |

3. Inhibition of Laser-induced thrombosis

The investigations of the compounds according to the invention in the model of Laser-induced thrombosis are carried out on male or female Sprague-Dawley rats with a body weight of about 200 g. The animals to be investigated are premedicated s.c. with 0.1 mg of atropine sulfate in solution, and anesthetized i.p. with 100 mg of ketamine hydrochloride and 4 mg of xylazine per kg of body weight. Arterioles from the mesentry, with a diameter of 12-25 μm, are used for the investigation. During the measurement, the exposed mesentry is hyperfused with warmed physiological NaCl (37° C.) or is covered with degassed liquid paraffin. The beam of a 4 W argon laser (supplied by Spectra Physics, Darmstadt, FRG) is introduced coaxially into the inverted ray path of a microscope (ICM 405, LD-Epilan 40/0.60; supplied by Zeiss, Oberkochen, FRG) by means of a ray adaptation and adjustment system (supplied by BIG, Munich, FRG). The wavelength used is 514.5 nm, with an energy above the objective of 40 mW. The single-shot exposure time is 1/15 sec. The diameter of the effective laser beam on the vessel is 10 μm, and with repeated exposure the next shot takes place 5 μm upstream in each case, directly on the vessel wall. All the measurement procedures are filmed by video camera (Sony, Trinicon tube) and stored on a recorder (Sony, U-matic 3/4). A survey image of the terminal vessels which are to be investigated is provided by the transillumination method using the same microscope with low magnification (LD-Epilan 8/0.20). A video-analyzer and a correlator are used to determine the rate of flow in the arterioles under investigation.

The test substances were administered orally in various doses in 0.9% sodium chloride solution (contained 1% carboxymethylcellulose, or in appropriate solubilizers) to the experimental animals one hour before the start of the experiment; control animals were treated in a corresponding manner, but without the test substances. The investigations were carried out with randomization as a double-blind study.

EVALUATION

The number of shots needed to induce a defined thrombus was counted. The frequency of the laser flashes was one lesion every 2 minutes, all the thrombi with a minimum size of ¼ of the vessel radius which were formed during the observation period being counted and measured. The results of the experiment were statistically analyzed using the $x^2$ test (L. Cavalli-Sforza, Biometrie, Stuttgart, 1969, pages 49 et seq.).

| Example | Number of laser shots to form a thrombus (compared with control) |   |
|---------|---------------------|---|
| 8       | 10 mg/kg p.o.       | +56% |

The compounds of the formula I specifically block the formation of thromboxane A₂ by inhibition of thromboxane synthetase, without affecting prostacyclin formation, and are thus suitable for the prevention or for the treatment of the abovementioned disorders which respond to inhibition of thromboxane synthetase.

The invention thus also relates to the use of the compounds of the formula I, and of their salts, for the treatment of the abovementioned disorders, and to pharmaceutical products based on the compounds according to the invention.

The compounds of the formula I are administered in various dosage forms, for example orally in the form of tablets, capsules or liquids, rectally in the form of suppositories, parenterally, subcutaneously or intramuscularly, preference being given to intravenous administration in emergency situations.

The compounds of the formula I, according to the invention can be used as free bases or in the form of their physiologically acceptable inorganic organic acid addition salts. The free bases and acid addition salts can be used in the form of their aqueous solutions or suspensions, or dissolved or suspended in pharmacologically acceptable organic solvents, such as monohydric or polyhydric alcohols such as, for example, ethanol, ethylene glycol or glycerol, in triacetin, in alcohol-/acetaldehyde diacetal mixtures, oils such as, for example, sunflower oil or fish live oil, ethers such as, for example, diethylene glycol dimethyl ether, or polyethers such as, for example, polyethylene glycol, or in the presence of other pharmacologically acceptable polymeric vehicles such as, for example, polyvinylpyrrolidone.

Suitable formulations are the customary pharmaceutical solutions for infusion or injection, and tablets, as well as formulations which can be used locally, such as creams, emulsions, suppositories or aerosols.

PREPARATION OF STARTING COMPOUNDS

EXAMPLE 1

2-Bromo-6-naphthyl methyl ketone ethylene acetal 19 g (76.3 mmol) of 2-bromo-6-acetylnaphthalene, 10.7 ml (11.76 g, 0.19 mol) of ethylene glycol and 250 mg of p-toluenesulfonic acid in 150 ml of toluene are heated under reflux with a water separtor until no further water separates out (about 1 hour). The toluene solution is extracted with saturated sodium bicarbonate solution, which in turn is reextracted twice with ethyl acetate. The combined organic phases are dried and evaporated in vacuo. 16.02 g (72%) of 2-bromo-6-naphthyl methyl ketone ethylene acetal are obtained from the residue by recrystallization from petroleum ether. Melting point 80°-2° C.

$^1$H-NMR (CDCl₃, 60 MHz) δ=1.7 (s, 3H; CH₃), 3.6–4.2 (m, 4H; —OCH₂—CH₂O—), 7.4–8.0 (m, 6H; arom. H)

EXAMPLE 2a

2-Acetyl-6-[1-hydroxy-1-(3-pyridyl)methyl]naphthalene 36.1 ml (57.75 mmol) of 1.6 M n-butyllithium in hexane are added dropwise, under argon, to a stirred solution of 16.1 g (55 mmol) of 2-bromo-6-napthyl methyl ketone ethylene acetal in 120 ml of absolute ether at −70° C. The mixture is then allowed to reach 0° C. and is stirred for one hour. Then, at −30° C., 6.19 g (57.75 mmol, 5.45 ml) of nicotinaldehyde in 15 ml of absolute ether are added dropwise. The mixture is subsequently allowed to reach room temperature within one hour, and is stirred for a further hour. After acidification to pH 1 with 2 N HCl the mixture is stirred overnight. After separation of the phases, the aqueous phase is extracted once with ether, the ether phase is discarded, and the aqueous phase is neutralized with sodium bicarbonate solution, which is then extracted with ethyl acetate. After drying and evaporation, the residue is recrystallized from isopropanol. 9.2 g (60%) of 2-acetyl-6-(1-hydroxy-1-(3-pyridyl) methyl(naphthalene are obtained. Melting point 157°–9° C.

$^1$H-NMR (CDCl$_3$, 60 MHz) δ=2.7 (s, 3H; CH$_3$), 3.2 (b, 1H; OH), 6.0 (s, 1H; CH), 7.0–8.6 (m, 10H; arom. H).

EXAMPLE 2b

2-Acetyl-6-[1-hydroxy-1-(3-pyridyl)ethyl]naphthalene is likewise obtained in analogy to 2a. Melting point 224°–7° C.

$^1$H-NMR (DMSO-d$_6$, 60 MHz) δ=2.0 (s, 3H; CH$_3$), 2.7 (b, 3H; C(O)CH$_3$), 6.1 (s, 1H; OH) 7.1–8.7 (m, 10H; arom. H).

EXAMPLE 2c

2-Acetyl-6-(1-hydroxy-1-phenyl-1-(3-pyridyl)methyl(naphthalene is obtained in analogy to 2a. Melting point 117°–120° C.

$^1$H-NMR (DMSO$_3$, 60 MHz) δ=2.7 (s, 3H; CH$_3$), 3.7 (b, 1H; OH), 7.0–8.6 (m, 15H; arom. H). Preparation of final products

EXAMPLE 3a

Methyl 6-(1-hydroxy-1-(3-pyridyl)methyl)-2-naphthoate 8.4 ml (66.2 mmol) of trimethylchlorosilane are added to 9.17 g (33.1 mmol) of 2-acetyl-6-(1-hydroxy-1-(3-pyridyl) methyl)naphthalene and 13.8 ml (99.3 mmol) of absolute triethylamine in 200 ml of absolute dichloromethane at 0° C., with stirring. After the mixture has stood at room temperature overnight, it is evaporated, the residue is taken up in sodium bicarbonate solution, and the solution is extracted with ethyl acetate. After drying and evaporation, the residue (12.4 g) is dissolved in 35 ml of dioxane and is added, at 0° to 10° C., to a solution of 14.2 g (0.355 mol) of sodium hydroxide in 70 ml of water, to which 5.5 ml (106.5 mmol, 17 g) of bromine have previously been added dropwise. After the mixture has stood overnight at room temperature, 10 ml of acetone are added, and the mixture is stirred for 30 minutes, extracted twice with ethyl acetate, and the aqueous phase is adjusted to pH 2 with 2 N HCl and is evaporated. The residue is then extracted by boiling with isopropanol and is evaporated. The remaining residue is taken up in 400 ml of 1 N methanolic hydrochloric acid, and the solution is allowed to stand at room temperature overnight. It is then evaporated, and the residue is taken up in sodium carbonate solution which is extracted with ethyl acetate. 4.4 g of crude product are obtained after drying and evaporation, from which 3.63 g (37%) of methyl 6-[1-hydroxy-1-(3-pyridyl) methyl]-2-naphthoate are isolated by chromatography on silica gel (ethyl acetate).

R$_F$ (ethyl acetate/methanol 8:1): 0.38; melting point 130°–5° C.

$^1$H-NMR (CDCl$_3$, 60 MHz) δ=2.8 (b, 1H; OH), 3.95 (s, 3H; CH$_3$), 6.0 (s, 1H; CH), 7.1–8.1 and 8.4–8.7 (m, 10H; arom. H).

EXAMPLE 3b

Methyl 6-[1-hydroxy-1-(3-pyridyl)ethyl]-2-naphthoate is obtained from 2-acetyl-6-(1-hydroxy-1-(3-pyridyl)ethyl) naphthalene in analogy to 3a, without it being necessary to protect the hydroxyl group as the trimethylsilyl ether.

R$_F$ (ethyl acetate/methanol 8:1): 0.4; melting point 190°–2° C.

$^1$H-NMR (CDCl$_3$, 60 MHz) δ=2.0 (s, 3H; C—CH$_3$); 2.5 (b, 1H; OH), 3.9 (s, 3H; OCH$_3$), 7.0–8.7 (m, 10H; arom. H).

EXAMPLE 3c

Methyl 6-[1-hydroxy-1-phenyl-1-(3-pyridyl)methyl]-2-naphthoate is prepared from 2-acetyl-6-(1-hydroxy-1-phenyl-1-(3-pyridyl) methyl)naphthalene in analogy to 3a without intermediate protection of the hydroxyl group as the trimethylsilyl ether. R$_F$ (ethyl acetate/methanol): 0.53.

$^1$H-NMR (CDCl$_3$, 60 MHz) δ=3.7 (b, 1H; OH), 3.95 (s, 3H; CH$_3$), 7.1–8.7 (m, 15H; arom. H).

EXAMPLE 4

Methyl 6-[1-methoxyimino-1-(3-pyridyl)methyl]-2-naphthoate (A) Methyl 6-(3-pyridylcarbonyl)-2-naphthoate 1.35 ml (4.16 g, 26 mmol) of bromine are added dropwise to 2.6 g (65 mmol) of sodium hydroxide in 20 ml of H$_2$O at 0° to 10° C. Then, at the same temperature, a solution of 1.8 g (6.5 mmol) of 2-acetyl-6-(1-hydroxy-1-(3-pyridyl)methyl] naphthalene in 10 ml of dioxane is added, and the mixture is stirred at room temperature for four hours. Then 2 ml of acetone are added, and the mixture is stirred for a further hour, and then the solution is extracted twice with ethyl acetate. The aqueous solution is acidified to pH 1 with concentrated HCl, evaporated to dryness in vacuo, and then the residue is extracted by boiling with isopropanol, and the isopropanol solution is evaporated in turn. The residue is taken up in 70 ml of 1 N methanolic HCl, and the solution is allowed to stand overnight. After evaporation, the residue is taken up in sodium bicarbonate solution, the solution is extracted with ethyl acetate, and the ethyl acetate is dried and evaporated in vacuo. 0.39 g (21%) of methyl 6-(3-pyridyl-carbonyl)-2-naphthoate is then isolated as an oil from the residue by chromatography on silica gel using ethyl acetate. R$_F$ (ethyl acetate/methanol 8:1): 0.5.

$^1$H-NMR (CDCl$_3$, 60 MHz) δ=4.0 (s, 3H; CH$_3$), 7.3–9.2 (m, 10H; arom. H).

(B) Methyl 6-[1-methoxyimino-1-(3-pyridyl)methyl]-2-naphthoate 280 mg (0.96 mmol) of methyl 6-(3-pyridylcarbonyl)-2-naphthoate and 0.8 g (9.6 mmol) of O-methylhydroxylamine hydrochloride in 4 ml of absolute pyridine are stirred at room temperature for four days. After evaporation, the residue is taken up in sodium chloride solution, and this is extracted with dichloromethane, which is dried and evaporated in vacuo. 0.29 g (94%) of methoxime is obtained as a mixture of two isomers, from which the major isomer can be isolated by crystallization from isopropanol. Melting point 146°–7° C.

$^1$H-NMR (CDCl$_3$, 60 MHz) $\delta$=3.95 and 4.05 (2x s, 6H; 2x CH$_3$), 7.3–8.9 (m, 10H; arom. H).

EXAMPLE 5

Methyl 6-(1-chloro-1-(3-pyridyl)methyl)-2-naphthoate 0.3 g (1.02 mmol) of methyl 6-[1-hydroxy-1-(3-pyridyl) methyl]-2-naphthoate and 0.349 g (1.33 mmol) of triphenyl-phosphine are dissolved in 3 ml of absolute Petrachloro-methane, and the solution is heated under reflux for three hours. It is then extracted with 2 N HCl, and the aqueous phase is neutralized with sodium bicarbonate solution and reextracted with ethyl acetate. After drying and evaporation in vacuo, the residue is chromatographed on silica gel using cyclohexane/ethyl acetate 1:1. 73 mg (23%) of methyl 6-[1-chloro-1-(3-pyridyl)methyl]-2-naphthoate are obtained as an oil.

R$_F$ (ethyl acetate): 0.45.

$^1$H-NMR (CDCl$_3$, 60 MHz) $\delta$=3.95 (s, 3H; CH$_3$), 6.3 (s, 1H; CH), 7.2–8.7 (m, 10H; arom. H).

EXAMPLE 6

Methyl 6-[1-(3-pyridyl)ethyl]-2-naphthoate (A) Methyl 6-[1-(3-pyridyl)ethenyl]-2-naphthoate 0.3 g (1 mmol) of methyl 6-[1-hydroxy-1-(3-pyridyl)ethyl]-2-naphthoate and 0.68 g (2.6 mmol) of triphenyl-phosphine in 3 ml of tetrachloromethane are heated under reflux for 9 hours. After evaporation, the residue is taken up in 4 N HCL, and triphenylphosphine and triphenylphosphine oxide are extracted with ethyl acetate. The aqueous phase is then neutralized with sodium bicarbonate. After extraction with ethyl acetate, and drying and evaporation of the ethyl acetate phase in vacuo, 0.25 g (86%) of methyl 6-[1-(3-pyridyl)ethenyl]-2-naphthoate is obtained as an oil. R$_F$(ethyl acetate/methanol 8:1): 0.59. $^1$H-NMR (CDCl$_3$, 60 MHz) $\delta$=4.0 (2, 3H; CH$_3$), 5.7 (d, 2H; C=CH$_2$), 7.0–8.7 (m, 10H; arom. H).

(B) Methyl 6-[1-(3-pyridyl)ethyl]-2-naphthoate 130 mg of Pd/C (10%) are added to 0.25 g (0.86 mmol) of methyl 6-[1-(3-pyridyl)ethenyl]-2-naphthoate in 25 ml of absolute methanol, and hydrogenation is carried out under atmospheric pressure (hydrogen uptake: 40 ml). The catalyst is then removed by filtration, and the solution is evaporated and chromatographed on silica gel using ethyl acetate. 50 mg (20%) of methyl 6-[1-(3-pyridyl)ethyl]-2-naphthoate are obtained as an oil. R$_F$ (ethyl acetate): 0.34.

$^1$H.NMR (CDCl$_3$, 60 MHz) $\delta$=1.75 (d, 3H; C—CH$_3$), 3.95 (s, 3H; OCH$_3$), 4.35 (q, 1H; CH), 7.0–8.6 (m, 10H; arom. H).

EXAMPLE 7

Methyl 6-[1-methoxy-1-(3-pyridyl) methyl]-2-naphthoate 52 mg (0.17 mmol) of methyl 6-[1-chloro-1-(3-pyridyl) methyl]-2-naphthoate and 8 mg (0.18 mmol) of sodium hydride dispersion (55%) in 4 ml of absolute methanol are heated under reflux for 6 hours. After the reaction mixture has been evaporated, the residue is taken up in sodium bicarbonate solution, which is extracted with ethyl acetate. After the ethyl acetate phase has been dried and evaporated in vacuo, the residue is chromatographed on silica gel using ethyl acetate. 48.2 mg (94%) of methyl 6-[1-methoxy-1-(3-pyridyl)methyl]-2-naphthoate are obtained. R$_F$ (ethyl acetate/cyclohexane 1:1): 0.17.

$^1$H-NMR (CDCl$_3$, 60 MHz) $\delta$=3.4 (s, 3H; ether–CH$_3$), 3.95 (s, 3H; ester–CH$_3$), 5.45 (s, 1H; CH), 7.1–8.7 (m, 10H; arom. H).

EXAMPLE 8

6-[1-Hydroxy-1-(4-methyl-3-pyridyl)methyl]-2-naphthoic acid hydrochloride 1.26 g (3.76 mmol) of isopropyl 6-[1-hydroxy-1-(4-methyl-3-pyridyl)methyl]-2-naphthoate are heated under reflux in 25 ml of 2 N HCL and 20 ml of concentrated HCL for three hours, then active charcoal is added and the mixture is filtered hot. The hydrochloride of the acid crystallizes out on cooling. After filtration with suction, washing with a little acetone and drying, 0.93 g (75%) of 6-[1-hydroxy-1-(4-methyl-3-pyridyl) methyl]-2-naphthoic acid hydrochloride is obtained. Melting point: 264°–7° C. (decomposition).

$^1$H-NMR (D$_2$O, 60 MHz) $\delta$=2.33 (s, 3H; CH$_3$), 6.25 (s, 1H; CH), 7.2–8.9 (m, 9H; arom. H).

EXAMPLE 9

The hydrochloride of 6-[1-hydroxy-1-(3-pyridyl)methyl]-2-naphthoic acid is prepared from methyl 6-[1-hydroxy-1-(3-pyridyl)methyl]-2-naphthoate in analogy to 8. Melting point 227°–9° C. (decomposition).

$^1$H-NMR (D$_2$O, 60 MHz) $\delta$=6.2 (s, 1H; CH), 7.3–8.9 (m, 10H; arom. H).

EXAMPLE 10

Isopropyl 6-[1-hydroxy-1-(4-methyl-3-pyridyl)methyl]-2-naphthoate 3.25 g (18.9 mmol) of 3-bromo-4-methylpyridine are initially introduced into 50 ml of absolute ether under argon and, at −70° C., 12.4 ml (19.8 mmol) of 1.6 M n-butyllithium solution in hexane are slowly added. The mixture is then stirred for 30 min., and, at −70° C., 5.43 g (20.8 mmol) of triisopropoxytitanium chloride in 20 ml of absolute ether are added dropwise. The reaction mixture is allowed to reach 0° C. and, at this temperature, it is added dropwise to a solution of 2.7 g (12.6 mmol) of methyl 6-formyl-2-naphthoate in 50 ml of absolute ether and 20 ml of absolute tetrahydrofuran.

The reaction mixture is stirred at room temperature until the aldehyde has completely reacted (~24 h). The mixture is diluted with 50 ml of ether and acidified to pH 1 with 2 N HCL. After extraction twice with ether, the aqueous phase is neutralized with saturated sodium bicarbonate solution. The precipitate is filtered off with suction and extracted by boiling with isopropanol and ethyl acetate. The organic phases are evaporated, and the residue is recrystallized from ethyl acetate. The mother liquor is chromatographed on silica gel using ethyl acetate/methanol (8:1). A total of 2.3 g (54%) of isopropyl 6-[1-hydroxy-1-(4-methyl-3-pyridyl)methyl]-2-naphthoate is obtained. Melting point 180°–3° C.

$^1$H-NMR (CDCl$_3$, 60 MHz) δ=1.4 (d, 6H; 1-propyl-CH$_3$), 2.2 (s, 3H; Ar-CH$_3$), 3.5 (b, 1H; OH), 5.3 (m, 1H; isopropyl-CH), 6.1 (s, 1H; Ar-C$\underline{H}$O), 6.9–8.6 (m, 9H; arom. H).

EXAMPLE 11

1-(6-Hydroxymethyl-2-naphthyl)-1-(4-methyl-3-pyridyl)-methanol 0.3 g (0.9 mmol) of isopropyl 6-[1-hydroxy-1-(4-methyl-3-pyridyl)methyl]-2-napthoate in 5 ml of absolute tetrahydrofuran is added, at 0° C., to 38 mg (1 mmol) of lithium alanate in 1 ml of absolute tetrahydrofuran, and the mixture is then stirred at room temperature (24 h). After addition of a further 40 mg (1 mmol) of lithium alanate the mixture is stirred at room temperature for 24 h. Excess lithium alanate is destroyed with 2 N HCl, and the solution is neutralized with sodium bicarbonate solution. It is extracted with ethyl acetate, and this is evaporated, and the residue is chromatographed on silica gel using ethyl acetate/methanol 4:1. 0.16 g (65%) of 1-(6-hydroxymethyl-2-naphthyl)-1-(4-methyl-3-pyridyl)methanol is obtained. Melting point 151°–3° C.

$^1$H-NMR (CD$_3$OD, 60 MHz) δ=2.3 (s, 3H; CH$_3$), 4.75 (s, 3H; CH$_2$ and OH), 6.1 (s, 1H; CH), 7.1–8.6 (m, 9H; arom. H).

We claim:
1. A compound of the formula I

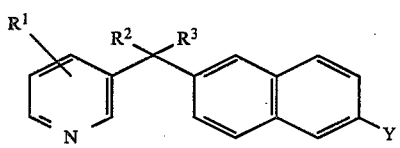

in which:
R$^1$ denotes hydrogen or, in the 2-, 4-, 5- or 6- position, halogen, a straight chain or branched alkyl radical having 1–6 carbon atoms, a cycloalkyl radical having 3–7 carbon atoms, a phenyl C$_1$–C$_2$-alkyl radical or a phenyl radical, each of which can be substituted 1–3 times in the phenyl nucleus by halogen, alkyl and/or alkoxy, each having 1–6 carbon atoms, or denotes a hydroxyl radical or an alkoxy radical having 1–6 carbon atoms, R$^2$ denotes a hydroxyl radical, halogen, an alkoxy radical having 1–6 carbon atoms, or a phenoxy radical which can be substituted 1–3 times in the phenyl nucleus by halogen, trifluoromethyl, alkyl and/or alkoxy, each having 1–6 carbon atoms, R$^3$ denotes hydrogen, a cycloalkyl radical having 3–7 carbon atoms, a straight-chain or branched alkyl radical having 1–8 carbon atoms, a straight-chain or branched unsaturated aliphatic hydrocarbon radical having up to 8 carbon atoms and up to 3 double or triple bonds, a phenyl radical which can be substituted 1–3 times in the phenyl nucleus by halogen, trifluoromethyl, hydroxyl, alkyl and/or alkoxy, each having 1–6 carbon atoms, or denotes a 2-, 3- or 4-pyridyl radical which can be substituted in the 4- or 5- position by C$_1$–C$_4$-alkyl, Y denotes a radical of the formula CO$_2$R$^5$,

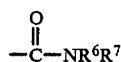

or CH$_2$OH,

R$^5$ denoting hydrogen, a straight chain or branched alkyl radical having up to 8 carbon atoms, a straight-chain or branched unsaturated aliphatic hydrocarbon radical having up to 6 carbon atoms, a cycloaliphatic hydrocarbon radical having 3 to 7 carbon atoms, an araliphatic hydrocarbon radical having 7 to 10 carbon atoms, or a physiologically tolerated metal ion, NH$_4$ ion or an ammonium ion which is derived from a primary, secondary or tertiary amine, or a tetraalkylammonium ion, R$^6$ denoting hydrogen, a straight chain or branched alkyl radical having 1–6 carbon atoms, a cycloaliphatic hydrocarbon radical having 3–7 carbon atoms, an araliphatic hydrocarbon radical which has 7–10 carbon atoms and can be substituted 1–3 times in the aryl nucleus by halogen, trifluoromethyl, alkyl and/or alkoxy, each having 1–6 carbon atoms, or denoting a phenyl radical which can be substituted 1–3 times in the phenyl nucleus by halogen, trifluoromethyl, alkyl and/or alkoxy, each having 1–6 carbon atoms, R$^7$ denoting hydrogen, a straight chain or branched alkyl radical having 1–6 carbon atoms, or R$^6$ and R$^7$ together denoting a —(CH$_2$)$_n$— group with n=3–6, or a —(CH$_2$)$_p$—Z—(CH$_2$)$_p$— group with p=2 or 3, Z being oxygen or N—R$^8$, R$^8$ denoting hydrogen or a straight-chain or branched alkyl radical having 1–6 carbon atoms, or a physiologically tolerated acid addition salt thereof, with the exception of the compounds of the formula 1 in which, when Y denotes the radicals —CONH$_2$ or COOR$^5$, with R$^5$ denoting hydrogen or C$_1$–C$_6$-alkyl, R$^1$ and R$^3$ represent hydrogen.

2. A compound of the formula I as claimed in claim 1, in which

R$^1$ denotes hydrogen or, in the 4- or 5-position, halogen, C$_1$–C$_4$-alkyl or C$_5$–C$_7$-cycloalkyl, R$^2$ denotes hydroxyl, halogen, C$_1$–C$_4$-alkoxy, unsubstituted phenoxy or phenoxy which is substituted 1–2 times by methyl, ethyl, methoxy, ethoxy, halogen or trifluoromethyl, R$^3$ denotes hydrogen, C$_1$–C$_6$-alkyl, C$_5$–C$_7$-cycloalkyl, unsubstituted phenyl or phenoxy which is substituted 1–2 times by methyl, ethyl, hydroxyl, methoxy, ethoxy, halogen or trifluoromethyl, or 3-pyridyl which can be substituted in the 4- or 5-position by methyl or ethyl, Y denotes —COOR$^5$,

or $CH_2OH$, $R^5$ representing hydrogen, $C_1$-$C_4$-alkyl, $C_2$-$C_4$-alkenyl, $C_5$-$C_7$-cycloalkyl, phenethyl, benzyl or a physiologically tolerated metal ion, $NH_4$ ion or substituted $NH_4$ ion, $R^6$ represents hydrogen, $C_1$-$C_4$-alkyl, cyclopentyl, cyclohexyl, phenyl, benzyl or phenethyl, and $R^7$ represents hydrogen or $C_1$-$C_4$ alkyl, or $R^6$ and $R^7$ together represent a $(CH_2)_n$ group with n=4 or 5, or a $-(CH_2)_2-O-(CH_2)_2-$ group, or a physiologically tolerated acid addition salt thereof.

3. A compound as claimed in claim 1, wherein in formula I $R^1$ denotes hydrogen, $C_1$-$C_2$-alkyl or phenyl, each in the 4-position, $R^2$ denotes hydroxyl, $C_1$-$C_2$-alkoxy or chlorine, $R^3$ denotes hydrogen or $C_1$-$C_2$-alkyl, and Y denotes the group $COOR^5$ with $R^5$ denoting hydrogen or $C_1$-$C_4$-alkyl.

4. A composition for use in inhibiting thromboxane synthetase which contains an amount of a compound as claimed in claim 1 effective to inhibit thromboxane synthetase together with pharmaceutically customary auxiliaries and vehicles.

* * * * *